(12) United States Patent
Kaneda

(10) Patent No.: US 10,697,922 B2
(45) Date of Patent: Jun. 30, 2020

(54) BIOSENSOR, PRODUCTION METHOD THEREOF, AND METHOD AND SYSTEM FOR MEASURING GLUCOSE OR LACTATE

(71) Applicant: ARKRAY, Inc., Kyoto-shi, Kyoto (JP)

(72) Inventor: Hisashi Kaneda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 156 days.

(21) Appl. No.: 15/719,428

(22) Filed: Sep. 28, 2017

(65) Prior Publication Data

US 2018/0095048 A1   Apr. 5, 2018

(30) Foreign Application Priority Data

Sep. 30, 2016  (JP) ................. 2016-193783

(51) Int. Cl.
*G01N 27/327* (2006.01)
*C12Q 1/26* (2006.01)
*C12Q 1/00* (2006.01)

(52) U.S. Cl.
CPC ......... *G01N 27/3272* (2013.01); *C12Q 1/004* (2013.01); *C12Q 1/005* (2013.01); *C12Q 1/006* (2013.01); *C12Q 1/26* (2013.01)

(58) Field of Classification Search
CPC .......................................... G01N 27/327–3278
USPC ....................... 204/403.01–403.15
See application file for complete search history.

(56) References Cited

U.S. PATENT DOCUMENTS

| 5,288,636 A | 2/1994 | Pollmann et al. |
| 2007/0034512 A1 | 2/2007 | Yamaoka et al. |
| 2009/0246808 A1 * | 10/2009 | Wilsey .................. C12Q 1/004 435/14 |
| 2013/0075276 A1 * | 3/2013 | Hoashi .................. C12Q 1/004 205/777.5 |
| 2015/0101929 A1 | 4/2015 | Jung et al. |
| 2016/0265021 A1 * | 9/2016 | Aiba .................... C12N 9/0006 |

FOREIGN PATENT DOCUMENTS

| EP | 2573190 A1 | 3/2013 |
| EP | 2573191 A1 | 3/2013 |
| EP | 2845908 A1 | 3/2015 |
| JP | H02-234697 A | 9/1990 |
| JP | H05-505459 A | 8/1993 |
| JP | H07-83871 A | 3/1995 |
| JP | 2008-521002 A | 6/2008 |

(Continued)

OTHER PUBLICATIONS

Extended European Search Report in European Patent Application No. 17194167.7 dated Nov. 29, 2017.

(Continued)

*Primary Examiner* — Bach T Dinh

(74) *Attorney, Agent, or Firm* — Morgan, Lewis & Bockius LLP

(57) ABSTRACT

Disclosed is a biosensor with improved humidity resistance that can be used as a glucose sensor or a lactate sensor. The biosensor includes: an insulative substrate; an electrode system having a working electrode and a counter electrode provided on the substrate; and a reagent layer provided on the electrode system. The reagent layer contains an oxidoreductase and 1-methoxy-5-methylphenazinium ethyl sulfate. This biosensor can be used as a glucose sensor or a lactate sensor.

20 Claims, 4 Drawing Sheets

(56) References Cited

FOREIGN PATENT DOCUMENTS

| JP | 2013-083634 A | 5/2013 |
|---|---|---|
| JP | 2015-517302 A | 6/2015 |
| WO | 91/09139 A1 | 6/1991 |
| WO | 2005/043146 A1 | 5/2005 |
| WO | 2006/057722 A1 | 6/2006 |
| WO | 2015/060150 A1 | 4/2015 |

OTHER PUBLICATIONS

Nakamura, S., et al., Use of 1-Methoxy-5-Methylphenazinium Methyl Sulfate (1-methoxyPMS) in the Assay of Some Enzymes of Diagnostic Importance, Clinica Chimica Acta 101:321-326, 1980.
Office Action issued in corresponding Japanese Patent Application No. 2016-193783 dated Mar. 5, 2020.

* cited by examiner

BIOSENSOR, PRODUCTION METHOD THEREOF, AND METHOD AND SYSTEM FOR MEASURING GLUCOSE OR LACTATE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present disclosure relates to a biosensor, particularly, a biosensor that can be used for measuring glucose or lactate, a production method thereof, a method and a system for measuring a glucose or lactate concentration.

Description of Related Art

Many of simple biosensors are based on electrochemical measurement. In a glucose sensor, a reagent containing an enzyme and a mediator as main components is provided on electrodes, a potential higher than an oxidation potential of the mediator is applied to the electrodes, and an electric current value obtained thereby is converted into a glucose value.

JP 1995(H7)-083871 A (Japanese Patent No. 3102613) relates to a biosensor. This document discloses phenazine methosulfate (PMS) as an exemplary mediator.

JP 2003-083634 A (Japanese Patent No. 5584740) relates to a glucose sensor containing *Aspergillus oryzae* type FAD-GDH. This document discloses that a combined use of a ruthenium compound and PMS as mediators enables efficient measurement of electric current values depending on glucose concentrations, whereas a use of either one of a ruthenium compound and PMS does not enable such measurement.

SUMMARY OF THE INVENTION

PMS is very unstable to light. It has been proposed to use, in place of PMS, 1-methoxy-5-methylphenazinium methyl sulfate (1-m-PMS) having higher light resistance than PMS. However, 1-m-PMS has low humidity resistance. Biosensors such as a glucose sensor and a lactate sensor are required to have storage stability because they are stored in various conditions, including high temperature, high humidity, etc. It was found that, when 1-m-PMS is used in dry-type biosensors, the sensors have a problem in humidity resistance.

The present disclosure provides a biosensor with improved humidity resistance, particularly, a biosensor that can be used as a glucose or lactate sensor, a production method thereof, a method and a system for measuring a glucose or lactate concentration.

The present disclosure, in one aspect, relates to a biosensor (also referred to as "biosensor of the present disclosure"), including: an insulative substrate; an electrode system having a working electrode and a counter electrode provided on the substrate; and a reagent layer provided on the electrode system. The reagent layer contains an oxidoreductase and 1-methoxy-5-methylphenazinium ethyl sulfate. A substance to be measured is glucose or lactate.

The present disclosure, in another aspect, relates to a method for measuring a concentration of glucose or lactate in a sample, the method including: bringing the sample into contact with an oxidoreductase; and electrochemically measuring a reaction between the glucose or lactate in the sample and the enzyme via 1-methoxy-5-methylphenazinium ethyl sulfate.

The present disclosure, in still another aspect, relates to a method for producing a biosensor for measuring glucose or lactate, the method including forming a reagent layer containing an oxidoreductase and 1-methoxy-5-methylphenazinium ethyl sulfate on an electrode system having a working electrode and a counter electrode provided on an insulative substrate.

The present disclosure, in still another aspect, relates to a concentration measurement system for measuring a concentration of glucose or lactate in a sample, the system including: the biosensor of the present disclosure; a means for applying a voltage to the electrode system in the biosensor; and a means for measuring an electric current in the electrode system.

The present disclosure, in one aspect, provides a biosensor with improved humidity resistance, a production method thereof, and a method and a system for measuring a glucose or lactate concentration.

DETAILED DESCRIPTION OF THE INVENTION

Figure 1A:
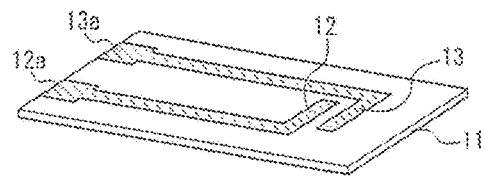
FIGS. 1A to 1F are schematic diagrams illustrating an example of a biosensor configuration and a method for producing the same.

The present disclosure, in one aspect, is based on the finding that methylphenazinium ethyl sulfate (PES) used as a mediator in the production of biosensor can improve the humidity resistance of glucose and lactate sensors, as compared with biosensors produced using methylphenazinium methyl sulfate (PMS).

The present disclosure, in one aspect, is based on the finding that using 1-methoxy-5-methylphenazinium ethyl sulfate as a mediator enables production of glucose and lactate sensors with improved humidity resistance, as compared with biosensors produced using 1-methoxy-5-methylphenazinium methyl sulfate.

Since the biosensor of the present disclosure has high humidity resistance, in one or more embodiments, it can produce effects of preventing the deterioration of sensor properties even when being left under high temperature and high humidity conditions and providing stable measurement under high temperature and high humidity circumstances.

[Biosensor]

The present disclosure, in one aspect, relates to a biosensor that includes: an insulative substrate; an electrode system having a working electrode and a counter electrode provided on the substrate; and a reagent layer provided on the electrode system. A substance to be measured for the biosensor of the present disclosure is glucose or lactate. The biosensor can be used as a glucose sensor or a lactate sensor.

The reagent layer contains an oxidoreductase (hereinafter, also referred to as "enzyme" simply) and 1-methoxy-5-methylphenazinium ethyl sulfate.

In the biosensor of the present disclosure, the oxidoreductase in one or more embodiments is, e.g., an oxidoreductase that can react with glucose or lactate. As the oxidoreductase, in one or more embodiments, any of those used in conventional glucose or lactate sensors or in glucose or lactate sensors to be developed in future can be used. The oxidoreductase in one or more embodiments includes glucose oxidase (GOD), glucose dehydrogenase (GDH), lactate oxidase (LOD), and lactate dehydrogenase (LDH). The GDH include GDHs containing various coenzymes, such as pyrrolo-quinoline quinone (PQQ)-GDH, flavin adenine dinucleotide (FAD)-GDH, nicotinamide adenine dinucleotide (NAD)-GDH, and nicotinamide adenine dinucleotide phosphate (NADP)-GDH.

The content of the oxidoreductase per one biosensor may be an amount of the same provided in a conventional glucose or lactate sensor or in a glucose or lactate sensor to be developed in future. The foregoing content is preferably 0.1 to 10 U, more preferably 0.2 to 6 U, and further preferably 0.5 to 4 U, from the viewpoint of the productivity (cost) and the maintenance of detection sensitivity. It should be noted that "U" referred to in the present disclosure is an enzyme unit, and an amount of the oxidoreductase to be reacted with 1 μmol of substrate at an optimum temperature in 1 minute. When the oxidoreductase is FAD-GDH, the enzyme unit "1 U" corresponds to the amount of the FAD-GDH that oxidizes 1 μmol of glucose at 37° C. in 1 minute.

The phrase "content per one biosensor" in the present disclosure refers to an amount used in a biosensor having one electrode system having a working electrode and a counter electrode, in one or more embodiments. The phrase refers to an amount contained in a reagent layer provided on one electrode system in another one or more embodiments. The phrase refers to an amount provided so that it is contained in a reaction system when a sample added (when the biosensor is used) in another one or more embodiments. A biosensor referred to in the phrase "content per one biosensor" in the present disclosure refers to a biosensor in a general size that is used with respect to a blood sample, in one or more embodiments. The general size is a size in the case where a blood sample added thereto is 0.2 to 1.0 μL, or 0.2 to 0.4 μL in one or more embodiments, or alternatively, it is a size in the case where a capacity of a reaction system that is formed by a blood sample in contact with a reagent layer is 0.2 to 1.0 μL in one or more embodiments. Therefore, regarding the "content per one glucose sensor", the range thereof disclosed in the present specification can be appropriately adjusted depending on the number of electrodes, and/or the capacity of a sample or a reaction system, in one or more embodiments.

When the oxidoreductase is GDH, the content of the GDH per one biosensor is preferably 0.2 to 10 U, more preferably 0.3 to 6 U, and further preferably 0.3 to 4 U, from the viewpoint of the productivity (cost) and the maintenance of detection sensitivity.

The reagent layer contains 1-m-PES. The content of 1-m-PES per one biosensor is preferably 30 to 1000 pmol, more preferably 40 to 800 pmol, and further preferably 50 to 500 pmol, from the viewpoint of the productivity (cost) and the detection sensitivity.

When the biosensor is a glucose sensor containing FAD-GDH and the content of 1-m-PES per one glucose sensor is 200 pmol, the content of FAD-GDH in one or more embodiments is 0.2 to 10 U.

The present disclosure may include an embodiment in which PES is used in place of 1-m-PES or PES is used together with 1-m-PES, in one or more embodiments.

The reagent layer in one or more embodiments may further contain a ruthenium compound. As the "ruthenium compound" in one or more embodiments, a ruthenium compound used as a mediator in a conventional glucose sensor or biosensor or in a glucose sensor or biosensor to be developed in future can be used. The ruthenium compound in one or more embodiments is preferably a ruthenium compound that can be present as an oxidized-type ruthenium complex in a reaction system. The type of a ligand of the ruthenium compound is not limited particularly as long as the ruthenium compound functions as a mediator (electron transmitter). An oxidized-type ruthenium complex expressed as the following chemical formula is preferably used, in one or more embodiments.

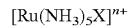

$$[Ru(NH_3)_5X]^{n+}$$

X in the chemical formula in one or more embodiments include $NH_3$, halogen ions, CN, pyridine, nicotinamide, and $H_2O$, among which $NH_3$ or halogen ions (e.g., $Cl^-$, $F^-$, $Br^-$, $I^-$) are preferably used. $n^+$ in the chemical formula represents the valence of the oxidized type ruthenium (III) complex determined depending on the type of X.

The content of the ruthenium compound per one biosensor in one or more embodiments may be an amount of the same provided in a conventional glucose or lactate sensor or in a glucose or lactate sensor to be developed in future. The content of the ruthenium compound is preferably 5 to 50 μg, more preferably 10 to 40 μg, and further preferably 15 to 25 μg, from the viewpoint of the productivity (cost) and the detection sensitivity.

When the biosensor is a glucose sensor containing FAD-GDH and the content of 1-m-PES per one glucose sensor is 200 pmol, the content of the FAD-GDH in one or more embodiments is 0.2 to 10 U, and the content of the ruthenium compound in one or more embodiments is 10 to 40 μg.

[Other Components Contained in the Reagent Layer]

The reagent layer in one or more embodiments may further contain a layered inorganic compound, a surfactant, a buffering agent, etc., from the viewpoint of improving the measurement sensitivity.

As the layered inorganic compound, in one or more embodiments, any of those used in conventional glucose or lactate sensors or in glucose or lactate sensors to be developed in future can be used. From the viewpoint described above, the layered inorganic compound is preferably any of swelling clay minerals having ion exchange capacity, more preferably any of bentonite, smectite, vermiculite, synthesized fluorine mica and the like, and further more preferably any of the following: synthetic smectites such as synthetic hectorite, synthetic saponite and the like; swelling synthetic micas such as synthetic fluorine mica; and synthetic micas such as Na type mica (natural mica is normally a non-swelling clay mineral). These layered inorganic compounds may be used alone, or in combination of two or more.

As the surfactant, any of those which can be used in conventional glucose or lactate sensors or in glucose or lactate sensors to be developed in future can be used. In one or more non-limiting embodiments, any of nonionic, anionic, cationic, and ampholytic surfactants can be used appropriately. Among these, ampholytic surfactants are preferred, from the viewpoint of improving the measurement sensitivity. The ampholytic surfactants in one or more embodiments include carboxybetaine, sulfobetaine, and phosphobetaine, among which sulfobetaine is preferred, from the same viewpoint as that described above. The sulfobetaine include 3-[(3-cholamidopropyl)dimethylammonio]propanesulfonate (CHAPS), 3-[(3-cholamidopropyl)dimethylammonio]-2-hydroxy-1-propanesulfonate (CHAPSO), and alkylhydroxysulfobetaine. Among these, CHAPS is preferred from the same viewpoint.

As the buffering agent, any of those which can be used in conventional glucose or lactate sensors or in glucose or lactate sensors to be developed in future can be used. In one or more non-limiting embodiments, an amine-based buffering agent and a buffering agent having a carboxyl group are preferred from the viewpoint of improving the measurement sensitivity. The amine-based buffering agent preferably used include, from the same viewpoint, Tris, ACES, CHES, CAPSO, TAPS, CAPS, Bis-Tris, TAPSO, TES, Tricine, and ADA Among these, ACES and Tris are more preferred, and ACES is further preferred. Preferably used as the buffering agent having the carboxyl group is any of an acetic acid-sodium acetate buffering agent, a malic acid-sodium acetate buffering agent, a malonic acid-sodium acetate buffering agent, and a succinic acid-sodium acetate buffering agent, from the same viewpoint, among which a succinic acid-sodium acetate buffering agent is more preferred. These buffering agents may be used alone, or in combination of two or more.

The above-described reagent layer in one or more embodiments may be a single layer structure in which all of reagents are contained, or may be a multilayer laminated structure in which one or more reagents are provided in separate layers. The multilayer laminated structure in one or more embodiments may be a laminated configuration in which an enzyme layer containing an enzyme is formed on an inorganic gel layer containing a layered inorganic compound. 1-m-PES in one or more embodiments is contained in at least one of the inorganic gel layer and the enzyme layer.

In the case of a single mediator using only 1-m-PES, the 1-m-PES in one or more embodiments is contained in at least one of the inorganic gel layer and the enzyme layer, preferably in the enzyme layer. In the case of double mediators using 1-m-PES and a ruthenium compound, the ruthenium compound and the 1-m-PES in one or more embodiments are contained separately in at least one of the inorganic gel layer and the enzyme layer, preferably, the ruthenium compound is contained in the inorganic gel layer and the 1-m-PES is contained in the enzyme layer.

The reagent layer is preferably provided in a dried state on an electrode system, from the viewpoint of the storage stability.

A biosensor of the present disclosure includes an insulative substrate, an electrode system having a working electrode and a counter electrode, and a reagent layer. The electrode system in one or more embodiments may have a reference electrode. Electrodes constituting the electrode system in one or more embodiments may be those which can be used in conventional glucose or lactate sensors or in glucose or lactate sensors to be developed in future. As the working electrode and the counter electrode, in one or more non-limiting embodiments, carbon electrodes may be used, or alternatively, metal electrodes made of platinum, gold, silver, nickel, palladium, or the like may be used. The reference electrode is not limited particularly, and a reference electrode that is generally used in electrochemical experiments or a reference electrode to be developed in future can be used. In one or more embodiments, however, a saturated calomel electrode, silver-silver chloride, etc., can be used, for example.

The electrode system is formed on an insulative substrate. As to a method for forming electrodes on an insulative substrate, in one or more embodiments, a printing technique such as photolithography, screen printing, gravure printing, or flexo printing can be used.

As to a material for the insulative substrate, materials that can be used in conventional glucose or lactate sensors or in glucose or lactate sensors to be developed in future can be used. In one or more non-limiting embodiments, the material for the insulative substrate include silicon, glass, glass epoxy, ceramic, polyethylene terephthalate (PET), polystyrene, polymethacrylate, polypropylene, acrylic resin, polyvinyl chloride, polyethylene, polypropylene, polyester, and polyimide.

Figure 1B:
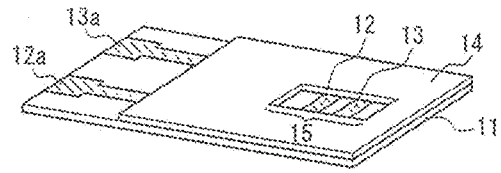
Figure 1C:
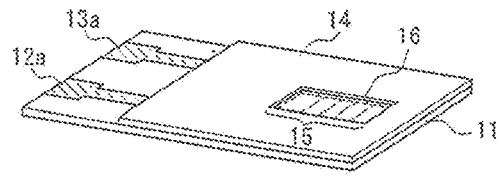
Figure 1D:
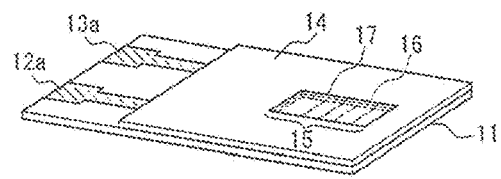
Figure 1E:
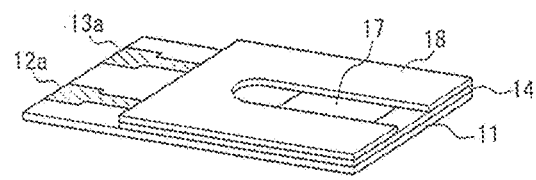

One embodiment of a biosensor of the present disclosure is explained with reference to FIGS. 1 and 2. FIG. 1 is perspective views showing a series of steps for producing the biosensor of the present embodiment. FIG. 2 is a cross-sectional view of the biosensor shown in FIG. 1(F), taken along an arrow line I-I, viewed in the arrow direction. In FIGS. 1 and 2, the same portions are denoted by the same reference numerals.

Figure 1F:
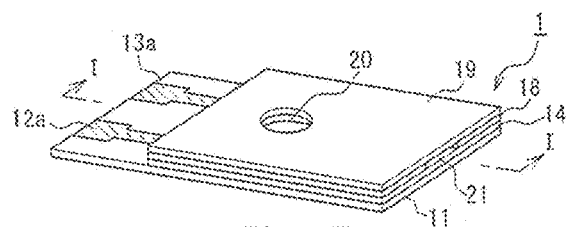
Figure 2:
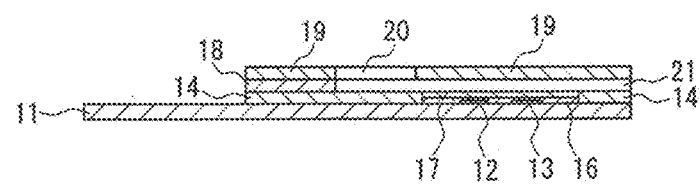
FIG. 2 is a schematic diagram illustrating an example of a biosensor configuration.

As shown in FIGS. 1(F) and 2, the biosensor of this embodiment includes a substrate 11; an electrode system composed of a working electrode 12 having a lead part 12a, and a counter electrode 13 having a lead part 13a; an insulative layer 14; an inorganic gel layer 16 containing a layered inorganic compound; an enzyme layer 17 containing an enzyme, a spacer 18 having an opening; and a cover 19 having a through hole 20. 1-m-PES is contained in at least one of the inorganic gel layer 16 and the enzyme layer 17.

As shown in FIG. 1(B), a detection section 15 is provided on one end part on one side (on the right side in FIGS. 1 and 2) of the substrate 11. In the detection section 15, the working electrode 12 and the counter electrode 13 are provided in parallel with each other, along a width direction of the substrate 11. One ends of the working electrode 12 and the counter electrode 13 are the lead parts 12a and 13a (on the left side in FIGS. 1 and 2), respectively, which are arranged perpendicular to the other ends of the working electrode 12 and the counter electrode 13 in the detection section 15 (FIG. 1(A)). A part between the working electrode 12 and the counter electrode 13 is insulative. On the substrate 11 provided with this electrode system, the insulative layer 14 is laminated, except for areas of the lead parts 12a and 13a and the detection section 15, as shown in FIG. 1(B). On the area of the detection section 15, where the insulative layer 14 is not laminated, the inorganic gel layer 16 and the enzyme layer 17 are laminated in this order. On the insulative layer 14, the spacer 18 having an opening corresponding to the detection section 15 is provided, as shown in FIG. 1(E). Further on the spacer 18, the cover 19 having the through hole 20 in an area corresponding to a part of the opening is provided (FIG. 1(F)). In a space of the opening, the enzyme layer 17 and a part that is interposed between the insulative layer 14 and the cover 19 becomes a sample supply section 21 in a capillary structure. The through hole 20 is an air hole for absorbing a sample by a capillary phenomenon.

The biosensor of this embodiment in one or more embodiments can be used in combination with measurement equipment provided with various means, for example, a means for applying a predetermined voltage for a certain set period, a means for measuring electric signals transmitted from the biosensor, a calculation means for calculating the electric signals into a concentration of a substance to be measured, etc.

An exemplary use of the biosensor of this embodiment is explained below.

First, a whole blood sample is brought into contact with an end of the opening (sample supply section 21) of the biosensor. Since the sample supply section 21 has a capillary structure as described above and the through hole 20 is provided in the cover 19 corresponding to the other end of the sample supply section 21, the sample is sucked into the inside of the sample supply section 21 due to the capillary phenomenon. The sample thus sucked permeates into the enzyme layer 17 provided on the detection section 15, dissolves an enzyme (an oxidoreductase) in the enzyme layer 17, and reaches a surface of the inorganic gel layer 16 below the enzyme layer 17. Then, reaction occurs among a substance to be measured (glucose or lactate) in the sample having reached the surface, the enzyme, and the 1-m-PES.

When the biosensor is prepared using a single mediator (1-m-PES only), a substance to be measured is oxidized by an enzyme, and electrons that migrate due to the oxidation reaction are transferred via 1-m-PES to the electrode positioned below the inorganic gel layer 16, whereby the concentration of the substance to be measured is measured.

When the biosensor is prepared using double mediators (e.g., 1-m-PES and an oxidized type ruthenium compound), a substance to be measured is oxidized by an enzyme, electrons that migrate due to the oxidation reaction are transferred via 1-m-PES to the oxidized type ruthenium compound, whereby a reduced type ruthenium (II) complex is formed. Then, electrons are exchanged between the reduced type ruthenium (II) complex and the electrode positioned below the inorganic gel layer 16, whereby the concentration of the substance to be measured is measured.

This embodiment exemplifies a case where the reagent layer has a structure of two layers composed of the inorganic gel layer 16 and the enzyme layer 17. However, the present disclosure is not limited to this case, and may have a single layer structure.

[Sample]

A sample in the biosensor of the present disclosure in one or more embodiments may be a biological sample such as blood, body fluid, urine, etc., or may be another liquid sample.

[Method for Producing Biosensor]

The present disclosure, in another aspect, relates to a method for producing a biosensor (also referred to as "production method of the present disclosure") that includes forming a reagent layer containing an oxidoreductase and 1-m-PES on an electrode system having a working electrode and a counter electrode provided on an insulative substrate. A biosensor obtained by the production method of the present disclosure can be used as a glucose sensor or a lactate sensor. In the production method of the present disclosure, the configurations and contents, etc., of the insulative substrate, the electrode system, and the reagent layer may be made identical to those described above.

[Method for Measuring a Glucose or Lactate Concentration]

The present disclosure, in another aspect, relates to a method for measuring a concentration of glucose or lactate in a sample (also referred to as "measurement method of the present disclosure"), the method including: bringing the sample into contact with an oxidoreductase; and electrochemically measuring a reaction between the glucose or lactate in the sample and the enzyme via 1-m-PES. In the measurement method of the present disclosure, the oxidoreductase is as exemplified above.

In the present disclosure, "electrochemically measuring" means measurement by applying an electrochemical measuring means, and it is, for example, the amperometric method, the potentiometric method, the coulometric analysis method, or the like, in one or more embodiments. The amperometric method is, for example, a method of measuring a value of an electric current generated when a reduced electron transfer substance, upon application of a voltage, is oxidized, in one or more embodiments.

An exemplary embodiment of the measurement method of the present disclosure is as follows: a reaction system including the sample, the oxidoreductase, and the 1-m-PES is directly provided on an electrode system having a working electrode and a counter electrode provided on an insulative substrate. Alternatively, another embodiment may be as follows: an inorganic gel layer is provided on the electrode system, and a reaction system including the sample and the oxidoreductase is provided on the inorganic gel layer. In this aspect, it is only required that the 1-m-PES be present in at least one of the inorganic gel layer and the reaction system.

In the case of the double mediators using 1-m-PES and a ruthenium compound, the ruthenium compound may be provided in the electrode system together with the 1-m-PES in the former embodiment. In the latter embodiment, the ruthenium compound may be provided in at least one of the inorganic gel layer and the reaction system separately from the 1-m-PES, preferably, the 1-m-PES is present in the reaction system and the ruthenium compound is present in the inorganic gel layer.

A preferable embodiment of the measurement method of the present disclosure is, for example, a glucose or lactate concentration measurement method using the biosensor of the present disclosure.

The measurement method of the present disclosure in another embodiment may include: applying a voltage to the electrode system of the biosensor after the contact between the sample and the enzyme; measuring a value of a response electric current discharged upon the application of the voltage; and calculating the concentration of the glucose or lactate in the sample based on the value of the response electric current. The voltage to be applied is not limited particularly, but in one or more embodiments, it is 10 to 700 mV, 50 to 500 mV, or 50 to 400 mV.

In the measurement method of the present disclosure, in another embodiment, a voltage may be applied to the electrode system after the electrode system is kept in a state without voltage application for a predetermined period after the sample and the enzyme are brought into contact, or alternatively, a voltage may be applied to the electrode system at the same time when they are brought into contact. The period while the electrode system is kept without voltage application is more than 0 second and not more than 30 seconds, or more than 0 second and not more than 10 seconds, in one or more embodiments.

The application of a voltage to the electrode system, the measurement of the response electric current value, and the calculation of the glucose or lactate concentration in the biosensor of the present disclosure and the measurement method of the present disclosure can be performed appropriately with use of a conventional glucose or lactate concentration measurement device, a glucose or lactate concentration measurement device to be developed in future, or the like.

[Glucose or Lactate Concentration Measurement System]

The present disclosure, in still another aspect, relates to a glucose or lactate concentration measurement system for measuring a concentration of glucose or lactate in a sample, the system including: the biosensor of the present disclosure; a means for applying a voltage to the electrode system of the biosensor; and a means for measuring an electric current in the electrode system.

The voltage application means is not particularly limited as long as it can be conductive with the electrode system of the biosensor and can apply a voltage thereto, and a known voltage application means or a voltage application means to be developed in future can be used. The voltage application means in one or more embodiments may include a contact that can be in contact with the electrode system of the biosensor, a power source such as a direct current power source, and the like.

The measurement means is intended to measure an electric current in the electrode system, generated upon the voltage application, and it may be anything as long as it is capable of measuring a value of a response electric current that is correlated with an amount of electrons discharged from the 1-m-PES, in some cases the ruthenium compound, in the reagent layer of the biosensor, in one or more embodiments. A measurement means used in a conventional biosensor or in a biosensor to be developed in future can be used.

The biosensor, the glucose or lactate concentration measurement method, and the glucose or lactate concentration measurement system are useful in the medical field and/or the scientific field such as non-remedial medicine, biochemistry, and biology.

The present disclosure may relate to one or more embodiments described below.

[1] A biosensor including:
an insulative substrate;
an electrode system having a working electrode and a counter electrode provided on the substrate; and
a reagent layer provided on the electrode system,
wherein the reagent layer contains an oxidoreductase and 1-methoxy-5-methylphenazinium ethyl sulfate, and
a substance to be measured is glucose or lactate.

[2] The biosensor according to [1], wherein the oxidoreductase is selected from the group consisting of glucose oxidase, glucose dehydrogenase, lactate oxidase, and lactate dehydrogenase.

[3] The biosensor according to [1] or [2], wherein the reagent layer further contains a ruthenium compound.

[4] The biosensor according to [3], wherein the ruthenium compound is a ruthenium compound represented by the following formula:

where X represents $NH_3$, a halogen ion, CN, pyridine, nicotinamide, or $H_2O$, and $n^+$ represents a valence of an oxidized type ruthenium (III) complex determined depending on the type of X.

[5] A method for measuring a concentration of glucose or lactate in a sample, the method including:
bringing the sample into contact with an oxidoreductase; and
electrochemically measuring a reaction between the glucose or lactate in the sample and the oxidoreductase via 1-methoxy-5-methylphenazinium ethyl sulfate.

[6] The measurement method according to [5], wherein the electrochemically measuring a reaction between the glucose or lactate in the sample and the oxidoreductase is performed via 1-methoxy-5-methylphenazinium ethyl sulfate and a ruthenium compound.

[7] The measurement method according to [5] or [6], performed with use of the biosensor according to any one of [1] to [4].

[8] The measurement method according to [7], further including:
applying a voltage to the electrode system of the biosensor after the contact between the sample and the oxidoreductase;
measuring a value of a response electric current discharged upon the application of the voltage; and
calculating the concentration of the glucose or lactate in the sample based on the value of the response electric current.

[9] A method for producing a biosensor for measuring glucose or lactate, the method including forming a reagent layer containing an oxidoreductase and 1-methoxy-5-methylphenazinium ethyl sulfate on an electrode system having a working electrode and a counter electrode provided on an insulative substrate.

[10] The production method according to [9], wherein the forming the reagent layer includes forming the reagent layer containing an enzyme such as the oxidoreductase, 1-methoxy-5-methylphenazinium ethyl sulfate, and a ruthenium compound.

[11] A concentration measurement system for measuring a concentration of glucose or lactate in a sample, the system including:
the biosensor according to any one of [1] to [4];
a means for applying a voltage to the electrode system in the biosensor; and
a means for measuring an electric current in the electrode system.

The following description further explains the present disclosure, by referring to Examples and Reference Examples. The interpretation of the present disclosure, however, may not be limited to the interpretation based on Examples shown below.

EXAMPLES

Example 1

A glucose sensor of Example 1 having the same structure as that shown in the schematic diagrams of FIGS. 1 and 2 was produced as described below.

First, a PET substrate (length: 50 mm, width: 6 mm, thickness: 250 μm) was prepared as the insulative substrate 11, and a carbon electrode system composed of the working electrode 12 and the counter electrode 13 having lead parts, respectively, was formed on one surface of the insulative substrate 11 by screen printing.

Next, the insulative layer 14 was formed in the following manner. First, an insulative resin polyester was dissolved in solvent carbitol acetate so as to have a concentration of 75 wt %, whereby an insulative paste was prepared. This insulative paste was applied by screen printing onto the insulative substrate 11, on which the electrode system was formed, and subjected to a heat treatment at 90° C. for 60 minutes, whereby the insulative layer 14 was formed. Part of the working electrode 12 and the counter electrode 13 as well as the lead parts 12a and 13a were not subjected to screen printing, so that the insulative layer 14 was not formed thereon. The part of the working electrode 12 and the counter electrode 13 where the insulative layer 14 was not formed was determined as the detection section 15.

Next, the inorganic gel layer 16 was formed on the detection section 15 in the following manner. First, an inorganic gel forming liquid (pH 7.5) containing synthetic smectite (trade name: "Lucentite SWN", manufactured by Co-op Chemical Co., Ltd.), sodium acetate, and succinic acid was prepared. This inorganic gel forming liquid was poured onto the detection section 15, and dried at 30° C., whereby the inorganic gel layer 16 was formed.

Further, the enzyme layer 17 was formed on the inorganic gel layer 16 in the following manner. First, an enzyme liquid containing GOD (trade name: "Amano "GO" AM, [GO-AM])", manufactured by Amano Enzyme, Inc.), 1-m-PES, and ACES buffering liquid (pH 7.5) was prepared. This enzyme liquid was poured onto the inorganic gel layer 16, and dried at 30° C., whereby the enzyme layer 17 was formed.

Finally, the spacer 18 having the opening was arranged on the insulative layer 14, and further, the cover 19 having the through hole 20 as an air hole was arranged on the spacer 18, whereby the glucose sensor of Example 1 was produced. Since a space of the opening of the spacer 18 interposed between the cover 19 and the insulative layer 14 had a capillary structure, this space was used as the sample supply section 21.

The contents of the GOD and the 1-m-PES per one glucose sensor of Example 1 were 2 U and 80 nmol, respectively. The enzyme unit "1 U" is an amount of the enzyme (GOD) that oxidizes 1 μmol of glucose at 37° C. in 1 minute.

Reference Example 1

A glucose sensor of Reference Example 1 was produced in the same manner as in Example 1 except that an enzyme liquid not containing 1-m-PES was used in the formation of the enzyme layer 17, and an inorganic gel forming liquid further containing a ruthenium compound ([Ru(NH$_3$)$_6$]Cl$_3$) was used in the formation of the inorganic gel layer 16.

The contents of the GOD and the ruthenium compound per one glucose sensor of Reference Example 1 were 2 U and 30 nmol, respectively.

Reference Example 2

A glucose sensor of Reference Example 2 was produced in the same manner as in Reference Example 1 except that the content of the ruthenium compound was 60 nmol, which is twice as much as that in Reference Example 1.

[Humidity Exposure Evaluation Test 1]

The glucose sensors of Example 1 and Reference Examples 1 and 2 were placed in an airtight container with water so as not to contact the water, and left to stand in an oven at 70° C. for four days for humidity exposure.

A voltage of 200 mV was continuously applied to the exposed glucose sensors for 5 seconds using a potentiostat, and the electric current values of the sensors upon application of the voltage were measured. As body samples, samples of venous whole blood (Hct 42%, pO$_2$ 70 mmHg) having an adjusted glucose concentration of 600 or 800 mg/dL were used. Table 1 below shows the results.

The same measurement was performed also for non-exposed glucose sensors of Example 1 and Reference Examples 1 and 2 that were not subjected to the above humidity exposure.

TABLE 1

| | Average electric current value (μA) (n = 5) | |
|---|---|---|
| | Glucose concentration 600 mg/dL | Glucose concentration 800 mg/dL |
| Example 1 | 2.27 | 2.48 |
| Reference Example 1 | 0.10 | 0.12 |
| Reference Example 2 | 0.13 | 0.12 |

Table 1 shows average electric current values (0.4 seconds after voltage application, μA) of the exposed glucose sensors (n=5). As shown in Table 1, the glucose sensor of Example 1 had a higher average electric current value after 4 days of humidity exposure than the glucose sensors of Reference Examples 1 and 2 (Table 1). In Reference Examples 1 and 2, the electric current value did not vary depending on the glucose concentration, whereas in Example 1, the electric current value varied depending on the glucose concentration. Moreover, in Example 1, an electric current falling rate from the average electric current value of the non-exposed glucose sensors was low. Therefore, the glucose sensor of Example 1 was confirmed to have higher humidity resistance than the glucose sensors of Reference Examples 1 and 2.

Moreover, it can be said that the glucose sensor of Example 1 can measure electric current values depending on glucose concentrations in body samples, even after 4 days of humidity exposure, as shown in FIG. 1.

Example 2

A glucose sensor of Example 2 was produced in the same manner as in Example 1 except that an inorganic gel forming liquid further containing a ruthenium compound ([Ru(NH$_3$)$_6$]Cl$_3$) was used in the formation of the inorganic gel layer 16, and FAD-GDH (trade name: "Glucose dehydrogenase (FAD-dependent) (GLD-351)", manufactured by TOYOBO Co., Ltd.) was used in place of GOD in the formation of the enzyme layer 17.

The contents of the FAD-GDH, the 1-m-PES, and the ruthenium compound per one glucose sensor of Example 2 were 3 U, 80 nmol, and 60 nmol, respectively. The enzyme unit "1 U" is an amount of the enzyme (FAD-GDH) that oxidizes 1 μmol of glucose at 37° C. in 1 minute.

Reference Example 3

A glucose sensor of Reference Example 3 was produced in the same manner as in Example 2 except that 1-m-PMS was used in place of 1-m-PES.

The contents of the FAD-GDH, the 1-m-PMS, and the ruthenium compound per one glucose sensor of Reference Example 3 were 3 U, 80 nmol, and 60 nmol, respectively.

[Reproductivity Confirmation Experiment]

Figure 3A:
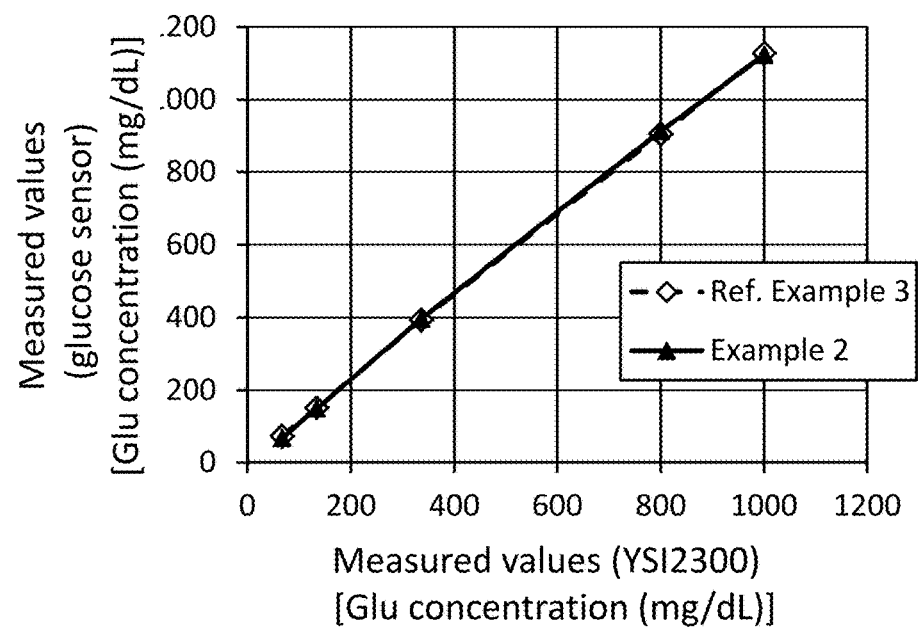
FIG. 3A is a graph showing an example of a relationship between glucose concentrations determined by glucose sensors of Examples 2 and Reference Example 3 and glucose concentrations determined by a marketed glucose analyzer.
Figure 3B:
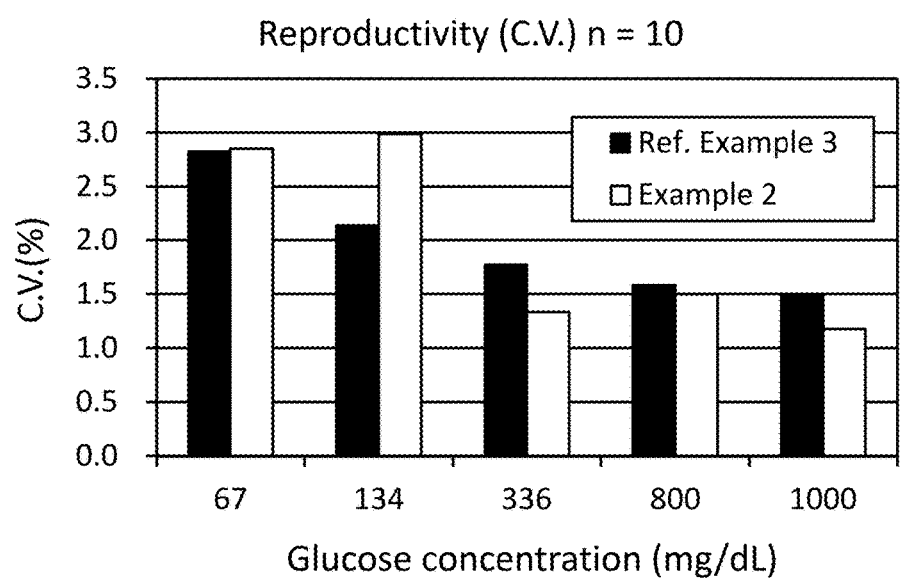
FIG. 3B is a graph showing an example of the reproductivity of glucose sensors of Example 2 and Reference Example 3.

A voltage of 200 mV was continuously applied to the glucose sensors of Example 2 and Reference Example 3 for 5 seconds using a potentiostat, and the electric current values of the sensors upon application of the voltage were measured. As body samples, samples of venous whole blood (Hct 42%, pO$_2$ 70 mmHg) having an adjusted glucose concentration of 67, 134, 336, 800 or 1000 mg/dL were used. FIGS. 3A and 3B show the results.

[Humidity Exposure Evaluation Test 2]

The glucose sensors of Example 2 and Reference Example 3 were placed on a weighing dish, and left to stand in a constant temperature and humidity chamber (40° C., 80% RH) for 1, 4, 8 or 24 hours for humidity exposure.

Figure 4A:
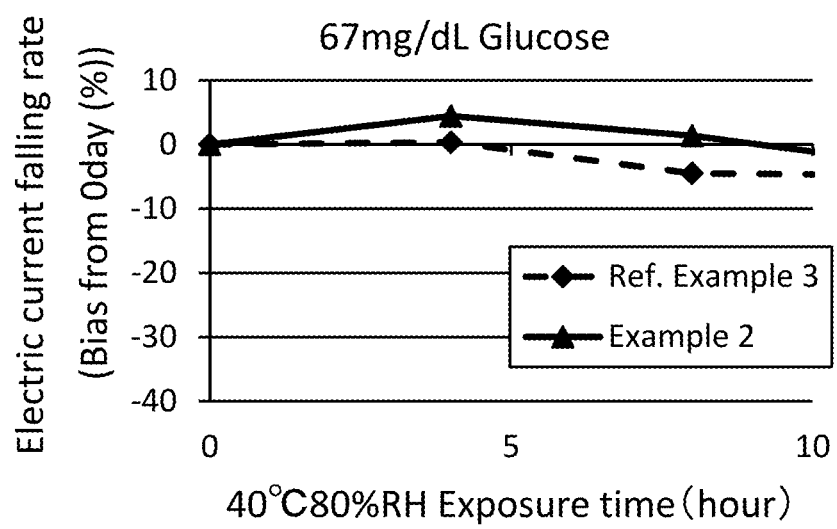
FIGS. 4A to 4C are graphs showing exemplary results of humidity exposure evaluation test on the glucose sensors of Examples 2 and Reference Example 3.
Figure 4B:
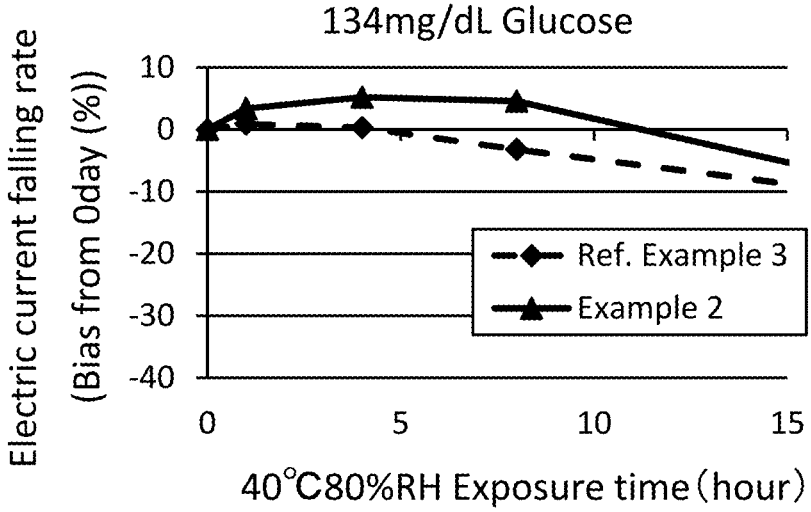
Figure 4C:
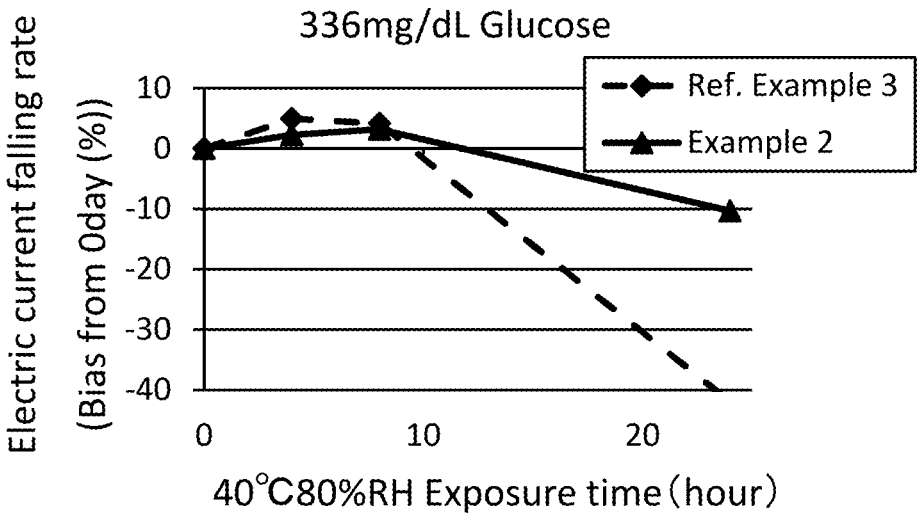

A voltage of 200 mV was continuously applied to the exposed and non-exposed glucose sensors for 5 seconds using a potentiostat, and the electric current values of the sensors upon application of the voltage were measured. As body samples, samples of venous whole blood (Hct 42%, pO$_2$ 70 mmHg) having an adjusted glucose concentration of 67, 134 or 336 mg/dL were used. FIGS. 4A to 4C show the results.

FIG. 3A is an exemplary graph (n=10) showing a correlation between glucose concentrations determined by the glucose sensors of Examples 2 and Reference Example 3 and glucose concentrations determined by a glucose & lactate analyzer (trade name: "YSI 2300", YSI Japan). FIG. 3B is an exemplary graph (n=10) showing the reproductivity of the glucose sensors of Example 2 and Reference Example 3. FIGS. 4A to 4C are exemplary graphs (n=10) showing a relationship between an exposure time and a bias (%) from the electric current value of the non-exposed glucose sensor ({(Electric current value of the exposed glucose sensor)−(Electric current value of the non-exposed glucose sensor)}/(Electric current value of the non-exposed glucose sensor)×100). FIGS. 4A to 4C show the results of the humidity exposure evaluation test 2 with glucose concentrations of 67, 134 and 336 mg/dL, respectively.

As shown in FIG. 3A, the glucose sensor of Example 2 achieved the same level of the glucose concentration measurement as the glucose sensor of Reference Example 3. As shown in FIG. 3B, the glucose sensor of Example 2 exhibited the same level of the reproductivity as the glucose sensor of Reference Example 3.

As shown in FIGS. 4A to 4C, the glucose sensor of Example 2 could prevent the decrease of the electric current value as compared with the glucose sensor of Reference Example 3. As shown in FIG. 4C, this effect was observed especially when the glucose concentration of the body sample was high. As described above, the constitution of the glucose sensor of Example 2 and that for the glucose sensor of Reference Example 3 were the same except that 1-m-PES was added in Example 2 and 1-m-PMS was added in Reference Example 3. The results of the humidity exposure evaluation test shown in FIGS. 4A to 4C confirmed that the 1-m-PES has more favorable humidity resistance than the 1-m-PMS. Further, the 1-m-PES exhibits favorable humidity resistance, even in the case of double mediators including the ruthenium compound.

Example 3

A lactate sensor of Example 3 was produced in the same manner as in Example 1 except that the inorganic gel layer 16 and the enzyme layer 17 were formed in the following manner.

An inorganic gel forming liquid (pH 7.5) containing synthetic smectite (trade name: "Lucentite SWN", manufactured by Co-op Chemical Co., Ltd.), a ruthenium compound ([Ru(NH$_3$)$_6$]Cl$_3$), sodium acetate, and succinic acid was prepared, and this inorganic gel forming liquid was poured onto the detection section 15 and dried at 30° C., whereby the inorganic gel layer 16 was formed.

An enzyme liquid containing LOD (trade name: "LOD-201", manufactured by TOYOBO Co., Ltd.), 1-m-PES, and ACES buffering liquid (pH 7.5) was prepared, and this enzyme liquid was poured onto the inorganic gel layer 16 and dried at 30° C., whereby the enzyme layer 17 was formed.

The contents of the LOD, the 1-m-PES, and the ruthenium compound per one lactate sensor of Example 3 were 2 U, 80 nmol, and 60 nmol, respectively. The enzyme unit "1 U" is an amount of the enzyme (LOD) that oxidizes 1 μmol of lactate at 37° C. in 1 minute.

Reference Example 4

A lactate sensor of Reference Example 4 was produced in the same manner as in Example 3 except that 1-m-PMS was used in place of 1-m-PES.

The contents of the LOD, the 1-m-PMS, and the ruthenium compound per one lactate sensor of Reference Example 4 were 3 U, 80 nmol, and 60 nmol, respectively.

It was confirmed that the lactate sensor of Example 3 achieved the same level of the lactate concentration measurement as the lactate sensor of Reference Example 4. Further, the lactate sensor of Example 3 exhibited the same level of the reproductivity as the lactate sensor of Reference Example 4.

[Humidity Exposure Evaluation Test 3]

The lactate sensors of Example 3 and Reference Example 4 were placed on a weighing dish, and left to stand in a constant temperature and humidity chamber (50° C., 80% RH) for 2 or 3 hours for humidity exposure.

Figure 5:
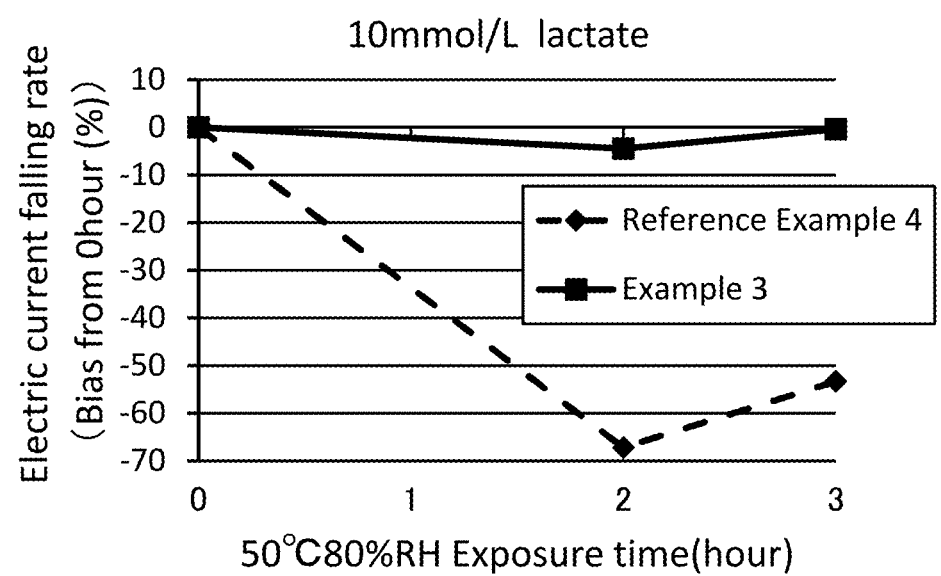
FIG. 5 is a graph showing exemplary results of humidity exposure evaluation test on lactate sensors of Examples 3 and Reference Example 4.

A voltage of 200 mV was continuously applied to the exposed and non-exposed lactate sensors for 7 seconds using a potentiostat, and the electric current values of the sensors upon application of the voltage were measured. As body samples, samples of venous whole blood (Hct 42%, pO$_2$ 70 mmHg) having an adjusted lactate concentration of 10 mmol/L were used. FIG. 5 shows the results.

FIG. 5 is an exemplary graph (n=5) showing a relationship between an exposure time and a bias (%) from the electric current value of the non-exposed lactate sensor (={(Electric current value of the exposed lactate sensor)−(Electric current value of the non-exposed lactate sensor)}/(Electric current value of the lactate sensor)×100). As shown in FIG. 5, the lactate sensor of Example 3 could significantly prevent the decrease of the electric current value as compared with the lactate sensor of Reference Example 4.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A biosensor for measuring glucose or lactate comprising:
   an insulative substrate;
   an electrode system comprising a working electrode and a counter electrode provided on the substrate; and
   a reagent layer provided on the electrode system,
   wherein the reagent layer comprises an oxidoreductase and 1-methoxy-5-methylphenazinium ethyl sulfate as a mediator.

2. The biosensor according to claim 1, wherein the oxidoreductase is selected from the group consisting of glucose oxidase, glucose dehydrogenase, lactate oxidase, and lactate dehydrogenase.

3. The biosensor according to claim 1, wherein the reagent layer further comprises a ruthenium compound.

4. The biosensor according to claim 3, wherein the ruthenium compound is represented by the following formula:

$$[Ru(NH_3)_5X]^{n+}$$

wherein X represents $NH_3$, a halogen ion, CN, pyridine, nicotinamide, or $H_2O$, and $n^+$ represents a valence of an oxidized type ruthenium (III) complex determined depending on the type of X.

5. The biosensor according to claim 1, wherein the content of 1-methoxy-5-methylphenazinium ethyl sulfate in the reagent layer is 30 to 1000 pmol.

6. The biosensor according to claim 1, wherein the reagent layer is a multilayer laminated structure in which an enzyme layer containing the oxidoreductase is formed on an inorganic gel layer containing a layered inorganic compound.

7. The biosensor according to claim 6, wherein the 1-methoxy-5-methylphenazinium ethyl sulfate is contained in the enzyme layer and, where present, a ruthenium compound is present in the inorganic gel layer.

8. A method for measuring a concentration of glucose or lactate in a sample, the method comprising:
bringing the sample into contact with an oxidoreductase; and
electrochemically measuring a reaction between the glucose or lactate in the sample and the oxidoreductase in the presence of 1-methoxy-5-methylphenazinium ethyl sulfate as a mediator.

9. The method according to claim 8, wherein the reaction between the glucose or lactate in the sample and the oxidoreductase is performed in the presence of 1-methoxy-5-methylphenazinium ethyl sulfate and a ruthenium compound as a mediators.

10. The method according to claim 8, wherein the oxidoreductase is selected from the group consisting of glucose oxidase, glucose dehydrogenase, lactate oxidase, and lactate dehydrogenase.

11. The method according to claim 9, wherein the ruthenium compound is represented by the following formula:

$$[Ru(NH_3)_5X]^{n+}$$

where X represents $NH_3$, a halogen ion, CN, pyridine, nicotinamide, or $H_2O$, and $n^+$ represents a valence of an oxidized type ruthenium(III) complex determined depending on the type of X.

12. The method according to claim 8 performed with use of a biosensor,
wherein the biosensor comprising:
an insulative substrate;
an electrode system comprising a working electrode and a counter electrode provided on the substrate; and
a reagent layer provided on the electrode system,
wherein the reagent layer comprises the oxidoreductase and 1-methoxy-5-methylphenazinium ethyl sulfate as a mediator.

13. The method according to claim 11, further comprising:
applying a voltage to the electrode system of the biosensor after the contact between the sample and the oxidoreductase;
measuring a value of a response electric current discharged upon the application of the voltage; and
calculating the concentration of the glucose or lactate in the sample based on the value of the response electric current.

14. The method according to claim 12, wherein the reagent layer further comprises a ruthenium compound.

15. The method according to claim 14, wherein the ruthenium compound is represented by the following formula:

$$[Ru(N H_3)_5X]^{n+}$$

where X represents $NH_3$, a halogen ion, CN, pyridine, nicotinamide, or $H_2O$, and $n^+$ represents a valence of an oxidized type ruthenium(III) complex determined depending on the type of X.

16. A method for producing a biosensor for measuring glucose or lactate, the method comprising forming a reagent layer containing an oxidoreductase and 1-methoxy-5-methylphenazinium ethyl sulfate as a mediator on an electrode system having a working electrode and a counter electrode provided on an insulative substrate.

17. The method according to claim 16, wherein the forming the reagent layer comprises forming the reagent layer comprising the oxidoreductase, 1-methoxy-5-methylphenazinium ethyl sulfate, and a ruthenium compound.

18. The method according to claim 16, wherein the oxidoreductase is selected from the group consisting of glucose oxidase, glucose dehydrogenase, lactate oxidase, and lactate dehydrogenase.

19. The method according to claim 17, wherein the ruthenium compound is represented by the following formula:

$$[Ru(N H_3)_5X]^{n+}$$

where X represents $NH_3$, a halogen ion, CN, pyridine, nicotinamide, or $H_2O$, and $n^+$ represents a valence of an oxidized type ruthenium(III) complex determined depending on the type of X.

20. A concentration measurement system for measuring a concentration of glucose or lactate in a sample, the system comprising:
the biosensor according to claim 1;
a power source for applying a voltage to the electrode system in the biosensor; and
measurement equipment for measuring an electric current in the electrode system.

* * * * *